United States Patent [19]

Mitsui et al.

[11] Patent Number: 5,013,755
[45] Date of Patent: May 7, 1991

[54] GERMICIDAL COMPOSITION

[75] Inventors: Susumu Mitsui, Koshigaya; Ryoji Funatsu, Tokyo; Shigeru Kurose, Misato, all of Japan

[73] Assignee: Somar Corporation, Japan

[21] Appl. No.: 426,161

[22] Filed: Oct. 25, 1989

[51] Int. Cl.$^5$ .............................................. A01N 37/10
[52] U.S. Cl. ........................................ 514/533; 71/67
[58] Field of Search ........................... 514/533; 71/67

[56] References Cited

U.S. PATENT DOCUMENTS 4,022,605 5/1977 Konya et al. ............................ 71/67

FOREIGN PATENT DOCUMENTS 2052989A 6/1980 United Kingdom.

OTHER PUBLICATIONS

Patent Abstracts of Japan, vol. 10, No. 203 (c–360) (2259), Jul. 16, 1986.
Patent Abstracts of Japan, vol. 8, No. 266 (c–255) (1703), Dec. 6, 1984.
Patent Abstracts of Japan, vol. 5, No. 180 (c–79) (852), Nov. 19, 1981.
Patent Abstracts of Japan, vol. 6, No. 25 (c–93) (913) Mar. 3, 1982.
Central Patents Index, Basic Abstracts Journal, Sec. C, Week 83/29, Sep. 14, 1983, Abstract No. 83-713774/29.

*Primary Examiner*—Stanley J. Friedman
*Assistant Examiner*—K. Weddington
*Attorney, Agent, or Firm*—Lorusso & Loud

[57] ABSTRACT

A germicidal composition is disclosed which includes: a first ingredient which is tribromoacetoxypropane of the formula:

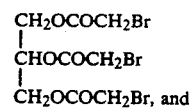

a second ingredient selected from the group consisting of (a) an alcohol of the general formula:

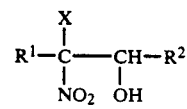

wherein $R^1$ and $R^2$ stand independently from each other for hydrogen, a halogen, an alkyl or a substituted alkyl and X stands for a halogen and (b) dibromocyanoacetamide of the formula:

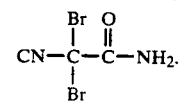

14 Claims, No Drawings

GERMICIDAL COMPOSITION

This invention relates generally to a germicide and, more specifically, to a germicidal composition suitable for preventing growth of germs such as yeasts and filamentous fungi in industrial water such as waste water from pulp mills or cooling water for heat exchangers.

In industrial water such as waste water from paper making steps in pulp-related industries and recirculating cooling water used in various mills, microorganisms such as germs, fungi and bacteria are apt to grow and to cause various problems.

For example, filamentous fungi and yeasts are apt to grow in industrial water used in paper or pulp mills and to form slime within water passages such as pipe walls having roughened surfaces and other portions such as chests and flow boxes through which the water is passed at a low flow rate. The accumulated slimes occasionally depart from their depositing surfaces to cause contamination of paper and pulp products. Other industrial products such as aqueous coating materials, polymer latex, bonding agents, metal machining oils, hides and skins also encounter similar problems. Further, accumulation of slimes also cause blockage of water passages and reduction of heat transfer efficiency.

To cope with these problems, there have been hitherto used organometallic compounds, chlorinated organic compounds, sulfur-containing organic compounds and quarternary ammonium compounds for the prevention of growth of germs in industrial water. These known germicides, however, have certain problems. That is, the known organometallic compounds and chlorinated organic compounds must be used in a large amount in order to obtain satisfactory germicidal effects. This causes environmental pollution. The known sulfur-containing organic compounds and quarternary ammonium compounds cause a problem of generation of unpleasant odor. Some of these compounds also cause a problem of foaming of the water to which they are added.

The present invention provides a germicidal composition comprising:

a first ingredient which is tribromoacetoxypropane of the formula:

CH$_2$OCOCH$_2$Br
|
CHOCOCH$_2$Br
|
CH$_2$OCOCH$_2$Br, and a second ingredient selected from the group consisting of (a) an alcohol of the general formula:

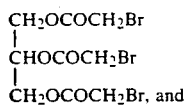

wherein R$^1$ and R$^2$ stand independently from each other for hydrogen, a halogen, an alkyl or a substituted alkyl and X stands for a halogen and (b) dibromocyanoacetamide of the formula:

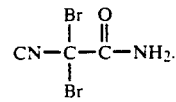

The present invention will now be described in detail below.

The first ingredient, tribromoacetoxypropane, is a compound known per se but by itself fails to exhibit satisfactory germicidal activities. The second ingredient, dibromocyanoacetamide or a specific aliphatic nitroalcohol, which is also a known compound, does not show satisfactory germicidal activities when used by itself, either. However, when the first and second ingredients are used in combination, the resulting composition exhibits an unexpectedly high synergistic germicidal activity and is effective in preventing growth of various germs inclusive of filamentous fungi, bacteria and yeasts.

Illustrative of suitable aliphatic nitroalcohol expressed by the above general formula are 2-chloro-2-nitroethanol, 1-chloro-1-nitro-2-propanol, 3-chloro-3-nitro-2-butanol, 2-chloro-2-nitro-1,3-butanediol, 1-chloro-1-nitro-2-butanol, 2-chloro-2-nitrobutanol, 2-chloro-2-nitro-3-pentanol, 2,2-dichloro-2-nitroethanol, 2-chloro-2-bromo-2-nitroethanol, 3-chloro-3-nitro-2,4-pentanediol, 4-chloro-4-nitro-3-hexanol, 2-bromo-2-nitroethanol, 2-bromo-2-nitro-3-propanol, 2-bromo-2-nitro-1,3-butanediol, 3-bromo-3-nitro-2,4-pentanediol, 2,2-dibromo-2-nitroethanol, 1,1-dibromo-1-nitro-2-propanol, 4-bromo-4-nitro-3-hexanol, 2-fluoro-2-nitroethanol, 2-fluoro-2-nitro-1,3-butanediol, 3-iodo-3-nitro-2-butanol, 2-fluoro-2-chloro-2-nitroethanol, 2-iodo-2-bromo-2-nitroethanol, 2-chloro-2-nitro-1,3-propanediol, 2-chloro-2-nitro-1,3-propanediol, 2-bromo-2-nitro-1,3-propanediol and mixtures thereof.

The first and second ingredients are used in such a proportion that the weight ratio of the first ingredient to the second ingredient is 1:100 to 100:1, preferably 1:50 to 50:1, more preferably 1:10 to 10:1.

The germicidal composition of the present invention may be in the form of a solution, a dispersion or an emulsion. Thus, a suitable liquid medium either aqueous or organic may be used for dissolving, dispersing or emulsifying the first and second ingredients. An emulsifier such as a surfactant or a stabilizer may be also be used to stabilize the dispersion or emulsion. Examples of organic media include alcohols, ketones, ethers and hydrocarbons.

Because of its high synergistic effect, a low concentration of the composition of the present invention can exhibit satisfactory germicidal activities. Thus, for example, when the composition is used for incorporation into industrial water of paper or pulp mills, a concentration of 0.01–100 ppm (calculated as a total amount of the first and second ingredients) is sufficient to obtain desired effect. For incorporation into industrial water for use in the field of aqueous coating materials, bonding starch or hides and skins, the concentration is generally 1–500 ppm.

The following examples will further illustrate the present invention. In the examples, "part" and "%" are by weight.

EXAMPLE 1

A germicide having the following composition was prepared:

| | |
|---|---|
| 2-Bromo-2-nitro-1,3-propanediol | 10 parts |
| Tribromoacetoxypropane | 10 parts |
| Diethyleneglycol monomethyl ether | 78 parts |
| Surfactant (Rapisol B-80, manufactured by Nihon Yushi K. K.) | 2 parts |

EXAMPLE 2

A germicide having the following composition was prepared:

| | |
|---|---|
| 2,2-Dibromo-2-nitroethanol | 10 parts |
| Tribromoacetoxypropane | 10 parts |
| Diethyleneglycol monomethyl ether | 78 parts |
| Surfactant (Rapisol B-80) | 2 parts |

EXAMPLE 3

A germicide having the following composition was prepared:

| | |
|---|---|
| 1,1-Dibromo-1-nitro-2-propanol | 10 parts |
| Tribromoacetoxypropane | 10 parts |
| Diethyleneglycol monomethyl ether | 78 parts |
| Surfactant (Rapisol B-80) | 2 parts |

EXAMPLE 4

A germicide having the following composition was prepared:

| | |
|---|---|
| 2,2-Dibromo-2-nitroethanol | 10 parts |
| Tribromoacetoxypropane | 15 parts |
| Diethyleneglycol monomethyl ether | 78 parts |
| Surfactant (Rapisol B-80) | 2 parts |

COMPARATIVE EXAMPLE 1

A germicide having the following composition was prepared:

| | |
|---|---|
| 2-Bromo-2-nitro-1,3-propanediol | 20 parts |
| Diethyleneglycol monomethyl ether | 78 parts |
| Surfactant (Rapisol B-80) | 2 parts |

COMPARATIVE EXAMPLE 2

A germicide having the following composition was prepared:

| | |
|---|---|
| 2,2-Dibromo-2-nitroethanol | 20 parts |
| Diethyleneglycol monomethyl ether | 78 parts |
| Surfactant (Rapisol B-80) | 2 parts |

COMPARATIVE EXAMPLE 3

A germicide having the following composition was prepared:

| | |
|---|---|
| 1,1-Dibromo-1-nitro-2-propanol | 20 parts |
| Diethyleneglycol monomethyl ether | 78 parts |
| Surfactant (Rapisol B-80) | 2 parts |

COMPARATIVE EXAMPLE 4

A germicide having the following composition was prepared:

| | |
|---|---|
| Tribromoacetoxypropane | 20 parts |
| Diethyleneglycol monomethyl ether | 78 parts |
| Surfactant (Rapisol B-80) | 2 parts |

EXAMPLE 5

A germicide having the following composition was prepared:

| | |
|---|---|
| 2,2-Dibromocyanoacetamide | 5 parts |
| Tribromoacetoxypropane | 25 parts |
| Diethyleneglycol monomethyl ether | 68 parts |
| Surfactant (Rapisol B-80) | 2 parts |

EXAMPLE 6

A germicide having the following composition was prepared:

| | |
|---|---|
| 2,2-Dibromocyanoacetamide | 25 parts |
| Tribromoacetoxypropane | 5 parts |
| Diethyleneglycol monomethyl ether | 68 parts |
| Surfactant (Rapisol B-80) | 2 parts |

COMPARATIVE EXAMPLE 5

A germicide having the following composition was prepared:

| | |
|---|---|
| Tribromoacetoxypropane | 30 parts |
| Diethyleneglycol monomethyl ether | 68 parts |
| Surfactant (Rapisol B-80) | 2 parts |

COMPARATIVE EXAMPLE 6

A germicide having the following composition was prepared:

| | |
|---|---|
| 2,2-Dibromocyanoacetamide | 30 parts |
| Diethyleneglycol monomethyl ether | 68 parts |
| Surfactant (Rapisol B-80) | 2 parts |

The above compositions were subjects to the following tests for evaluating their germicidal properties.

ACTIVITY TEST

The following germs were used (Indicated in the brackets are abbreviations):

| | |
|---|---|
| *Pseudomonas aeruginosa* | (P.a) |
| *Aerobactor aerogenes* | (A.a) |
| *Bacillus subtillis* | (B.s) |
| *Alcaligenes viscoses* | (A.v) |
| *Aspergillus niger* | (A.n) |

-continued

| Geotrichum sp. | (G.s) |

Each germ was suspended in an aqueous culture medium containing 0.1% peptone, 0.05% glucose, 0.01% potassium hydrogen phosphate and 0.005% magnesium sulfate. A predetermined amount of the suspension was sampled in test tubes to which a predetermined amount (5, 10, 20, 40 and 80 ppm) of the germicidal composition to be tested was mixed. The mixture was cultured with shaking at 32° C. for 24 hours. Thereafter, the degree of growth of the germ was measured by measurement of turbidity. The concentration of the germicidal composition which perfectly prevented the growth of the germ was as shown in Table 1. Each germ was found to grow upon culturing in the absence of the germicide.

TABLE 1

| Example | P.a | A.a | B.s | A.v | A.n | G.s |
|---|---|---|---|---|---|---|
| 1 | 5 | 10 | 5 | 10 | 10 | 10 |
| 2 | 5 | 5 | 5 | 5 | 5 | 5 |
| 3 | 5 | 5 | 5 | 5 | 5 | 5 |
| 4 | 10 | 10 | 10 | 10 | 5 | 5 |
| Comp. 1 | 20 | 40 | 20 | 40 | 80 | 80 |
| Comp. 2 | 10 | 20 | 10 | 20 | 80 | 80 |
| Comp. 3 | 10 | 20 | 10 | 20 | 40 | 40 |
| Comp. 4 | 80 | 80 | 40 | 40 | 40 | 40 |
| 5 | 10 | 10 | 10 | 5 | 5 | 5 |
| 6 | 5 | 5 | 5 | 5 | 10 | 10 |
| Comp. 5 | 80 | 80 | 40 | 40 | 40 | 40 |
| Comp. 6 | 20 | 20 | 20 | 20 | 80 | 80 |

From the results shown in Table 1, it will be appreciated that the germicidal compositions of the present invention can prevent any of the tested germs from growing with a low concentration of 10 ppm or less.

GROWTH PREVENTING TEST (1)

To a recirculating white liquor used in a paper making step of a paper mill was added each of the above germicidal compositions three times per day (2 hours in one time) so that the concentration of the germicide in the white liquor was maintained at 20 ppm. The test was carried out continuously for 7 days. Then the white liquor was sampled to measure the number of germ cells. Thus, the sampled white liquor was diluted with sterilized water and poured into a glass tray in a predetermined amount, to which a Waxman agar culture medium was poured. After gentle mixing, the mixture was allowed to be solidified with a flattened surface and placed in an incubator at 32° C. for 2 days for culturing. Then the colony was counted by a colony counter to give the results shown in Table 2. During the 7 days test, the number of the occurrence of paper breakage in the paper making step was counted. The results are also shown in Table 2.

TABLE 2

| Example No. | Number of Cells (per 1 ml) | Number of Occurrence of Paper Breakage |
|---|---|---|
| 1 | $3.0 \times 10^2$ | 1 |
| 2 | $10^2$ or less | 0 |
| 3 | $10^2$ or less | 0 |
| 4 | $10^2$ or less | 0 |
| Comp. 1 | $4.5 \times 10^5$ | 9 |
| Comp. 2 | $6.0 \times 10^4$ | 6 |
| Comp. 3 | $7.6 \times 10^4$ | 6 |
| Comp. 4 | $3.6 \times 10^3$ | 10 |
| 5 | $10^2$ or less | 0 |
| 6 | $10^2$ or less | 0 |
| Comp. 5 | $4.8 \times 10^6$ | 9 |

TABLE 2-continued

| Example No. | Number of Cells (per 1 ml) | Number of Occurrence of Paper Breakage |
|---|---|---|
| Comp. 6 | $8.5 \times 10^5$ | 6 |
| Control* | over $10^9$ | 15 |

*no germicidal was used.

GROWTH PREVENTING TEST (2)

To an aqueous paper coating liquid (pH 10.0) of a starch type was added a bouillon liquid medium and a previously rotted, paper coating liquid, to which was added each of the germicidal compositions to a concentration of 300 ppm. The resulting mixture was incubated at 32° C. for 5 days and the number of the living cells was counted. The results are shown in Table 3.

TABLE 3

| Example No. | Number of Cells (per 1 ml) |
|---|---|
| 1 | $10^2$ or less |
| 2 | $10^2$ or less |
| 3 | $10^2$ or less |
| 4 | $10^2$ or less |
| Comp. 1 | $3.6 \times 10^5$ |
| Comp. 2 | $6.2 \times 10^3$ |
| Comp. 3 | $8.8 \times 10^3$ |
| Comp. 4 | $4.8 \times 10^7$ |
| 5 | $10^2$ or less |
| 6 | $10^2$ or less |
| Comp. 5 | $2.8 \times 10^6$ |
| Comp. 6 | $3.8 \times 10^4$ |
| Control* | $1.6 \times 10^9$ |

*no germicide was used

What is claimed is:

1. A germicidal composition comprising:
a first ingredient which is tribromoacetoxypropane of the formula:

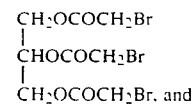

$$CH_2OCOCH_2Br$$
$$CHOCOCH_2Br$$
$$CH_2OCOCH_2Br, \text{ and}$$

a second ingredient selected from the group consisting of (a) an alcohol of the general formula:

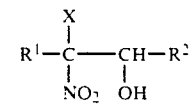

$$R^1-\underset{\underset{NO_2}{|}}{\overset{\overset{X}{|}}{C}}-\underset{\underset{OH}{|}}{CH}-R^2$$

wherein $R^1$ and $R^2$ stand independently from each other for hydrogen, a halogen, an alkyl or a substituted alkyl and X stands for a halogen and (b) dibromocyanoacetamide of the formula:

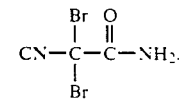

$$CN-\underset{\underset{Br}{|}}{\overset{\overset{Br}{|}}{C}}-\overset{\overset{O}{\|}}{C}-NH_2.$$

2. A germicidal composition according to claim 1, wherein the weight ratio of the first ingredient to the second ingredient is 100:1 to 1:100.

3. A germicidal composition according to claim 1, wherein the weight ratio of the first ingredient to the second ingredient is 50:1 to 1:50.

4. A germicidal composition according to claim 1, wherein the weight ratio of the first ingredient to the second ingredient is 10:1 to 1:10.

5. A germicidal composition according to claim 1, wherein the second ingredient is an alcohol selected from the group consisting of 2-chloro-2-nitroethanol, 1-chloro-1-nitro-2-propanol, 3-chloro-3-nitro-2-butanol, 2-chloro-2-nitro-1,3-butanediol, 1-chloro-1-nitro-2-butanol, 2-chloro-2-nitrobutanol, 2-chloro-2-nitro-3-pentanol, 2,2-dichloro-2-nitroethanol, 2-chloro-2-bromo-2-nitroethanol, 3-chloro-3-nitro-2,4-pentanediol, 4-chloro-4-nitro-3-hexanol, 2-bromo-2-nitroethanol, 2-bromo-2-nitro-3-propanol, 2-bromo-2-nitro-1,3-butanediol, 3-bromo-3-nitro-2,4-pentanediol, 2,2-dibromo--2-nitroethanol, 1,1-dibromo-1-nitro-2-propanol, 4-bromo-4-nitro-3-hexanol, 2-fluoro-2-nitroethanol, 2-fluoro-2-nitro-1,3-butanediol, 3-iodo-3-nitro-2-butanol, 2-fluoro-2-chloro-2-nitroethanol, 2-iodo-2-bromo-2-nitroethanol, 2-chloro-2-nitro-1,3-propanediol, 2-chloro-2-nitro-1,3-propanediol and 2-bromo-2-nitro-1,3-propanediol.

6. A germicidal composition according to claim 1, further comprising a liquid medium in which the first and second ingredients are dispersed, emulsified or dissolved.

7. A germicidal composition according to claim 1, wherein said second ingredient is an alcohol of the general formula:

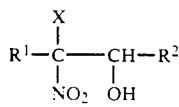

wherein $R^1$ stands for halogen or hydroxy lower alkyl, $R^2$ stands for hydrogen or lower alkyl and X stands for halogen.

8. A germicidal composition according to claim 1, wherein said second ingredient is an alcohol of the general formula:

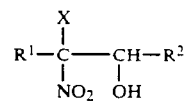

wherein $R^1$ stands for Br, Cl, $HOCH_2-$ or $CH_3CH(OH)-$, $R^2$ stands for hydrogen or methyl and X stands for Br or Cl.

9. A germicidal composition according to claim 7, wherein the weight ratio of the first ingredient to the second ingredient is 100:1 to 1:100.

10. A germicidal composition according to claim 8, wherein the weight ratio of the first ingredient to the second ingredient is 100:1 to 1:100.

11. A germicidal composition according to claim 7, wherein the weight ration of the of the first ingredient to the second ingredient is 50:1 to 1:50.

12. A germicidal composition according to claim 8, wherein the weight ratio of the of the first ingredient to the second ingredient is 50:1 to 1:50.

13. A germicidal composition according to claim 7, wherein the weight ratio of the of the first ingredient to the second ingredient is 10:1 to 1:10.

14. A germicidal composition according to claim 8, wherein the weight ratio of the of the first ingredient to the second ingredient is 10:1 to 1:10.

* * * * *

UNITED STATES PATENT AND TRADEMARK OFFICE
CERTIFICATE OF CORRECTION

PATENT NO. : 5,013,755
DATED : May 7, 1991
INVENTOR(S) : MITSUI et al

It is certified that error appears in the above-identified patent and that said Letters Patent is hereby corrected as shown below:

On the title page, please insert the following:

--Foreign Application Priority Data

October 27, 1988 [JP] Japan............... 63-272794

October 27, 1988 [JP] Japan............... 63-272793--

Signed and Sealed this

Twenty-second Day of December, 1992

Attest:

DOUGLAS B. COMER

*Attesting Officer*      *Acting Commissioner of Patents and Trademarks*